(12) United States Patent
Larson et al.

(10) Patent No.: US 8,114,142 B2
(45) Date of Patent: Feb. 14, 2012

(54) CATHETER

(75) Inventors: Karen Larson, Lino Lakes, MN (US); Gary Pederson, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1105 days.

(21) Appl. No.: 11/094,022

(22) Filed: Mar. 30, 2005

(65) Prior Publication Data

US 2006/0229698 A1    Oct. 12, 2006

(51) Int. Cl.
*A61F 2/06*    (2006.01)
(52) U.S. Cl. ...................................................... 623/1.11
(58) Field of Classification Search ............... 623/1.11, 623/1.12; 604/171, 172, 158–163
See application file for complete search history.

(56) References Cited

U.S. PATENT DOCUMENTS

| | | | |
|---|---|---|---|
| 3,957,054 A | 5/1976 | McFarlane | |
| 4,406,656 A | 9/1983 | Hattler et al. | |
| 4,955,862 A * | 9/1990 | Sepetka | 604/164.13 |
| 5,125,909 A * | 6/1992 | Heimberger | 604/264 |
| 5,244,619 A * | 9/1993 | Burnham | 264/171.2 |
| 5,343,771 A * | 9/1994 | Turriff et al. | 73/864.44 |
| 5,571,086 A * | 11/1996 | Kaplan et al. | 604/96.01 |
| 5,593,394 A | 1/1997 | Kanesaka et al. | |
| 5,647,846 A * | 7/1997 | Berg et al. | 604/93.01 |
| 5,674,240 A * | 10/1997 | Bonutti et al. | 606/198 |
| 5,681,296 A * | 10/1997 | Ishida | 604/523 |
| 5,882,347 A | 3/1999 | Mouris-Laan et al. | |
| 6,364,897 B1 * | 4/2002 | Bonutti | 606/232 |
| 6,537,205 B1 * | 3/2003 | Smith | 600/104 |
| 6,579,221 B1 | 6/2003 | Peterson | |
| 6,623,491 B2 * | 9/2003 | Thompson | 606/108 |
| 6,623,518 B2 | 9/2003 | Thompson et al. | |
| 6,786,918 B1 * | 9/2004 | Krivoruchko et al. | 623/1.11 |
| 6,893,421 B1 | 5/2005 | Larson et al. | |
| 7,130,700 B2 * | 10/2006 | Gardeski et al. | 607/122 |
| 7,146,869 B2 * | 12/2006 | Miyaguchi et al. | 74/89.32 |
| 2002/0095203 A1 * | 7/2002 | Thompson et al. | 623/1.11 |
| 2003/0023298 A1 | 1/2003 | Jervis | |
| 2003/0144731 A1 * | 7/2003 | Wolinsky et al. | 623/1.16 |
| 2004/0167385 A1 * | 8/2004 | Rioux et al. | 600/373 |
| 2005/0049609 A1 | 3/2005 | Gunderson et al. | |
| 2005/0166695 A1 * | 8/2005 | Yabe et al. | 74/424.88 |

FOREIGN PATENT DOCUMENTS

| | | |
|---|---|---|
| DE | 28 20 239 | 11/1978 |
| EP | 1385450 | 3/2007 |
| WO | WO 02/056953 | 7/2002 |

OTHER PUBLICATIONS

International Search Report and Written Opinion, PCT/US2006/012369, mailed Jan. 16, 2007.

* cited by examiner

*Primary Examiner* — Gary Jackson
*Assistant Examiner* — Eric Blatt
(74) *Attorney, Agent, or Firm* — Seager, Tufte & Wickhem, LLC (57) ABSTRACT

Catheters, as well as related systems and methods are disclosed.

23 Claims, 9 Drawing Sheets

CATHETER

TECHNICAL FIELD

This invention relates to systems for delivering medical devices, as well as related systems and methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer member surrounding a catheter with a stent positioned therebetween. Generally, the operator of the system positions the distal portion within the lumen at a desired location (e.g., so that the stent is adjacent an occlusion). The operator can then retract the sheath to allow the stent to engage the occlusion/lumen wall. Thereafter, the operator removes the distal portion of the system from the lumen.

SUMMARY

In general, the invention relates to systems for delivering medical devices, as well as related systems and methods. The systems can be used as, for example, implantable medical endoprosthesis delivery systems (e.g., stent delivery systems). The systems can be used, for example, to deploy a medical endoprosthesis (e.g., a stent) at a desired location within a lumen of a subject (e.g., an artery of a human).

In some embodiments, the systems include an outer member and an inner member at least partially surrounded by the outer member. One or more inserts can be operatively associated with the inner member. For example, the inserts can be at least partially disposed in sockets of the inner member. One or more, e.g., all, of the sockets can be configured as a slot or groove extending along at least a portion of the inner member. In some embodiments, one or more, e.g., all, of the sockets have a generally uniform, e.g., circular, cross section. In general, the portion of the insert disposed in a socket has a shape complementary to the socket.

In some embodiments, the lubricity of the insert is different from the lubricity of the inner member. For example, the insert can be formed of a polymeric material, e.g., a fluorinated polymer, that is more lubricious than the inner member.

In some embodiments, the one or more inserts can reduce limit or prevent contact between an inner surface of the outer member and the inner member. During deployment, the systems can allow for a relatively low-force withdrawal of the outer member relative to the inner member. This can reduce stretching of the outer member and compression of the inner member, which can enhance deployment accuracy.

Other features and advantages of the invention will be apparent from the description, drawings and claims.

DESCRIPTION OF DRAWINGS

FIG. 4b is an end-on cross section through the endoprosthesis delivery system of FIG. 4a.

FIG. 4c is a perspective view of an insert of the endoprosthesis delivery system of FIG. 4a.

FIG. 4d is a partial side view of a catheter of the endoprosthesis delivery system of FIG. 4a.

FIGS. 5a-5d are side cross-sectional views of different embodiments of inserts.

Like reference symbols in the various drawings indicate like elements.

DETAILED DESCRIPTION

Figure 1:
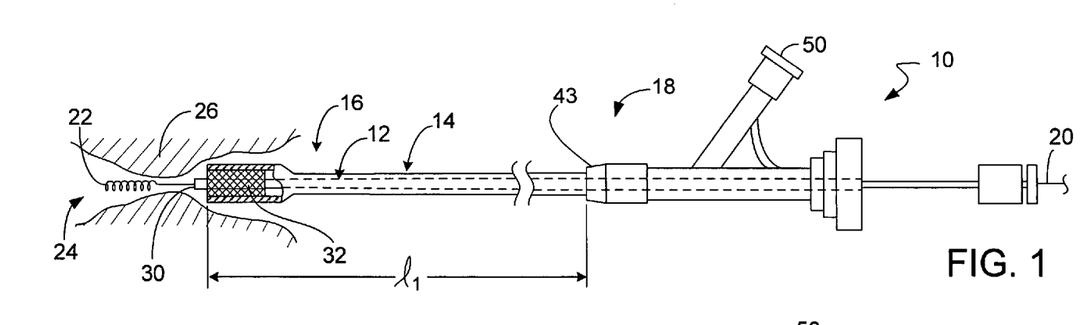
FIGS. 1-3 are side views of an embodiment of an endoprosthesis delivery system during use.
Figure 2:
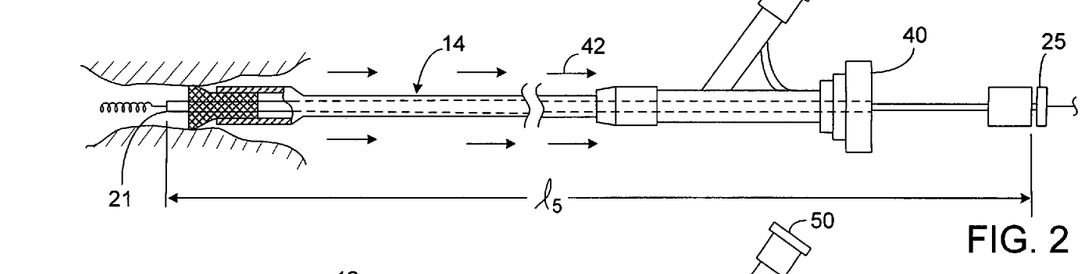
Figure 3:
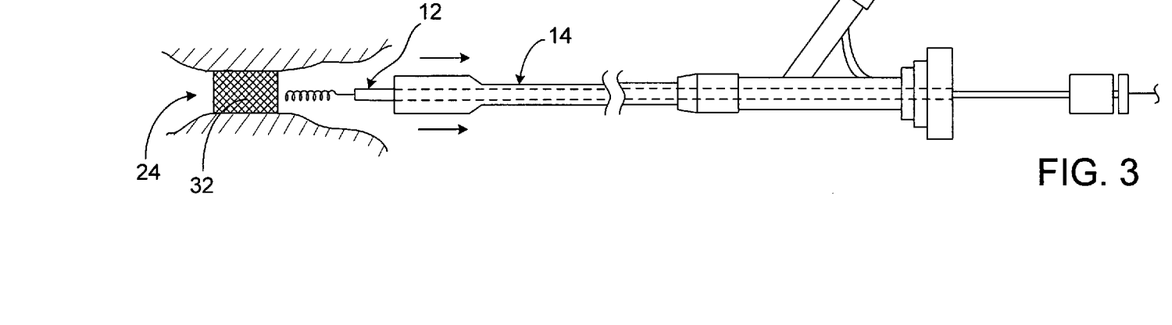

FIGS. 1-3 show an implantable medical endoprosthesis delivery system 10 that includes a catheter 12, an outer member 14 surrounding catheter 12, and a stent 32 positioned between catheter 12 and outer member 14. The delivery system 10 includes a distal end 16 dimensioned for insertion into a body lumen (e.g., an artery of a human) and a proximal end 18 that resides outside the body of a subject, and that contains at least one port 49 and lumens for manipulation by a physician. In an exemplary use of system 10, a guide wire 20 with a blunted end 22 is inserted into a body lumen 24 by making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, catheter 12, stent 32 and outer member 14 are placed over the proximal end of guide wire 20. Catheter 12, stent 32 and outer member 14 are moved distally over guide wire 20 and positioned within lumen 24 so that stent 32 is adjacent constricted site 26 of lumen 24. Outer member 14 is moved proximally, allowing stent 32 to expand and engage constricted site 26. Outer member 14, catheter 12 and guide wire 20 are removed from body lumen 24, leaving stent 32 engaged with constricted site 26.

Figure 4A:
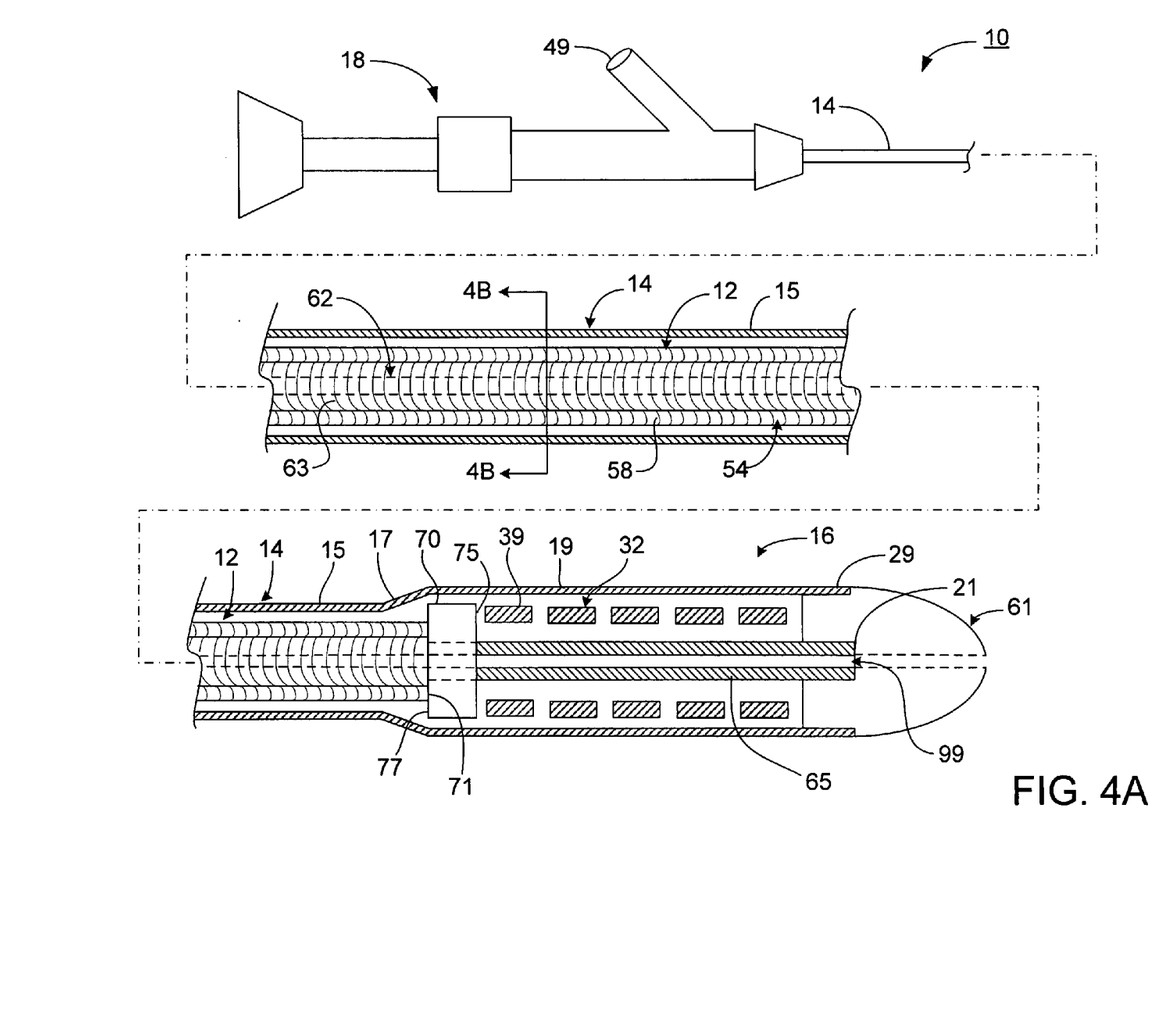
FIG. 4a is an exploded, mixed view of an embodiment of an endoprosthesis delivery system.

Referring also to FIG. 4a, outer member 14 includes a proximal outer member portion 15 joined by a transition outer member portion 17 to a distal outer member portion 19, which has a distal end 29. Outer member 14 defines a length l between its distal end 29 and a proximal fitting 43 (FIG. 1). Catheter 12 includes a tube 62 having a proximal tube portion 63 and a distal tube portion 65, which has a distal end 21. Stent 32 is housed between the distal outer member portion 19 and the distal tube portion 65. A guide wire lumen 99 extends through tube 62 and through a distal tip 61 secured about distal end 21 to assist navigation of the delivery system through body lumen 24.

A bumper 70 is secured about tube 62 proximal to stent 32. During withdrawal of outer member 14, friction between outer member 14 and stent 32 can urge the endoprosthesis proximally against a distal face 75 of bumper 70. Hence, bumper 70 can limit or prevent proximal movement of stent 32.

Figures 4B, 5A, 5B:
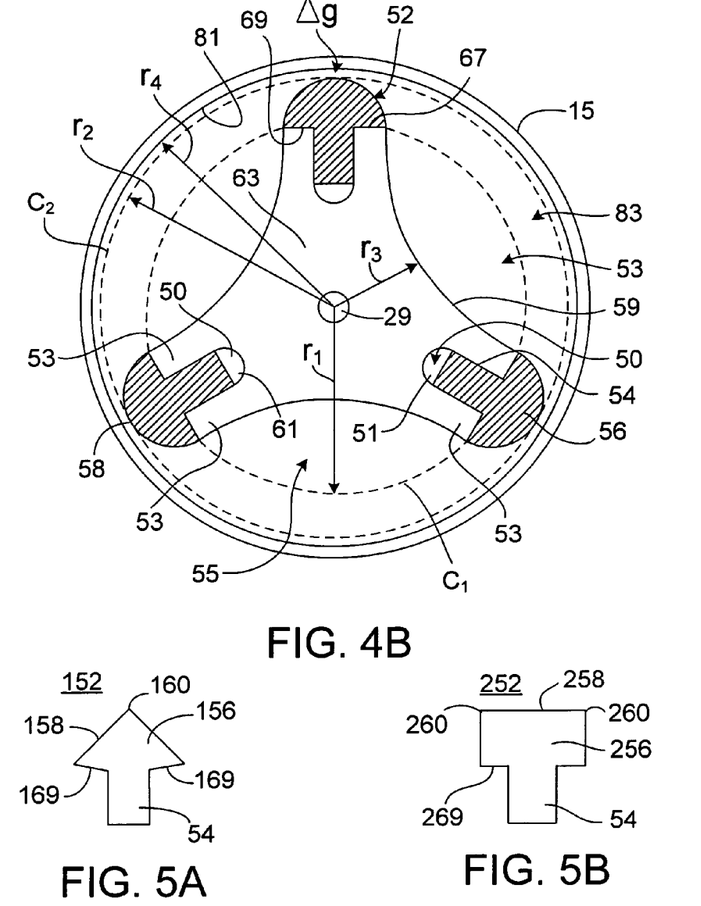
Figure 4C:
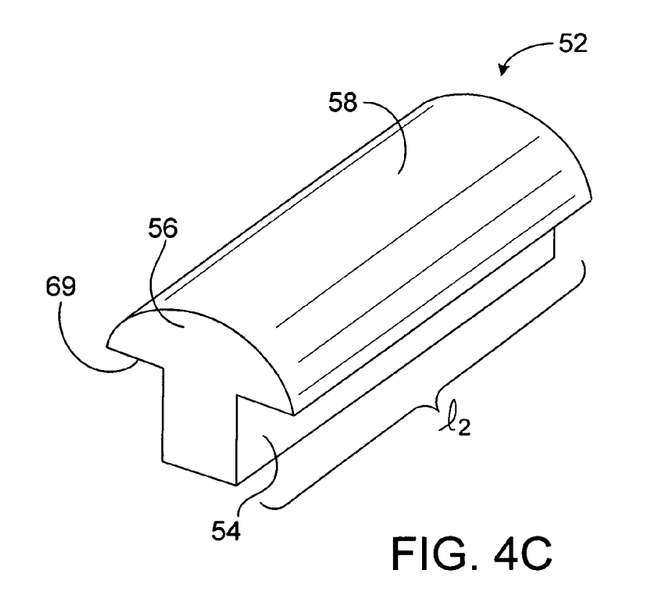
Figure 4D:
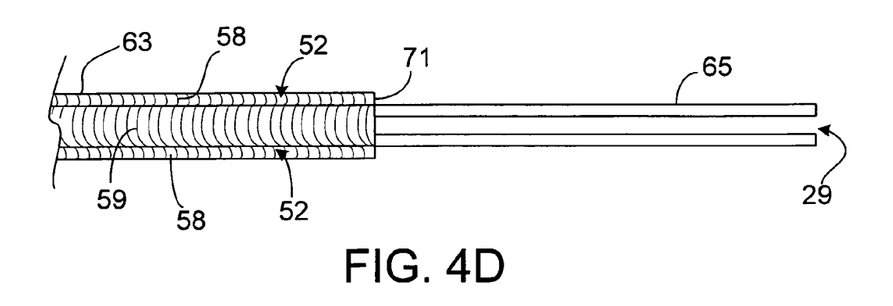

Referring also to FIGS. 4b-4d, proximal tube portion 63 defines a plurality of sockets 50. Sockets 50 have a slot or groove-like shape 51 defined by a pair of splines 53 extending longitudinally along at least a portion of tube 62. An insert 52 is operatively associated with each socket 50. For example, each insert has a projecting portion 56 and a tongue 54 disposed within its corresponding socket. Inserts 52 define a length l2 (FIG. 4c) and extend along at least a portion of tube 62 (FIG. 4a).

An outer surface 67 of splines 53 defines a maximum radial extent r1 of proximal tube portion 63. Taken together, outer surfaces 67 of splines 53 define a circumference c1. Adjacent pairs of splines 53 are spaced apart by a depression 55 defined between an outer surface 59 of proximal tube portion 63 and circumference c1, i.e., circumference c2 is greater than circumference c1. A minimum radial extent r3 of proximal tube outer surface 59 is smaller than the radial extent r1 of splines 53.

Inserts 52 have a maximum radial extent r2 defined by an insert outer surface 58. Taken together, insert outer surfaces 58 define a circumference c2. Radial extent r2 of insert outer surfaces 58 is greater than maximum radial extent r1 of the proximal tube portion 63. Hence, projecting portions 56 project radially outward of proximal tube portion 63.

Proximal outer member portion 15 has an inner radial extent r4 defined by an inner surface 81. Inner radial extent r4 is somewhat larger than maximum radial extent r2 of inserts 52 so that a small gap Δg can form between inner surface 81 and each insert outer surface 58. Inner surface 81, insert outer surfaces 58, and proximal tube outer surface 59 define channels 83 extending longitudinally between at least a portion of outer member 14 and tube 62. Fluid, e.g., saline or radiopaque fluid can be introduced into system 10, e.g., through port 49, and can travel along the channels.

Tongue 54 of each insert 52 extends only partially into socket 50 leaving an unoccupied void 61 within socket 50 (FIG. 4b). The presence of void 61 can enhance the flexibility of proximal tube portion 63 by reducing the amount of material of the proximal tube portion 63. Projecting portion 56 is wider than tongue 54 in at least one dimension so as to define shoulders 69. Each shoulder 69 can rest upon a respective outer surface 67 of splines 53, which can provide radial compression resistance to projecting portion 56 of insert 52.

As seen in FIG. 4a, inserts 52 extend longitudinally with respect to tube 62. In some embodiments, inserts 52 extend along the entire length of proximal tube portion 63. In some embodiments, length l2 of inserts 52 is at least about 5%, e.g., at least about 10%, at least about 25%, at least about 50% as long as a length l5 of catheter 12 between distal end 21 and a proximal end 25 (FIG. 2). In some embodiments, inserts 52 extend for substantially all or all of the length l5 of the tube 62. In some embodiments, length l2 of inserts 52 is at least about 5%, e.g., at least about 10%, at least about 25%, at least about 50% as long as length $l_1$ of outer member 14. Sockets 50 can have a length similar to the length of an insert received therein or the sockets can have a larger length such as to receive more than one insert. Length l2 of inserts 52 can be the same or different for inserts of a given system.

Inserts 52 can limit or prevent contact between an interior of outer member 14 and tube 62, e.g., during navigation of system 10 through body lumen 24 and/or during proximal withdrawal of outer member 14. For example, as seen in FIG. 4b, inserts 52 are disposed between outer surfaces 67 of splines 53 and inner surface 81 of proximal outer member portion 15. Hence, contact can instead occur between inserts 52 and outer member 14, e.g., between outer surfaces 58 of inserts 52 and inner surface 81 of proximal outer member portion 15.

Inserts 52 can be formed of a material having a lubricity different from a lubricity of tube 62, e.g., different from a lubricity of proximal tube portion 63. In some embodiments, inserts 52 have a higher lubricity than tube 62. A coefficient of friction, e.g., a static coefficient of friction, between inserts 52 and the inner surface of outer member 14 may be lower than a coefficient of friction between tube 62 and the inner surface of outer member 14. Hence, the presence of inserts 52 can reduce a withdrawal force of outer member 14 with respect to inner catheter 12.

In some embodiments, inserts 52 are formed of a lubricious polymer, e.g., a fluoropolymer (e.g., PTFE), a polyacetal (e.g., Delrin), a polyamide (e.g., Nylon), or combination thereof. Insert lubricity can be enhanced by an additive e.g., a fluoropolymer, a silicone, an ultrahigh molecular weight polyethylene, an oil, or blends thereof.

Inserts 52 may be formed partially or wholly of other polymeric materials. Examples of suitable polymeric materials include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyeolefins (e.g., Marlex® polyethylene, Marlex® polypropylene), HDPEs, low-density polyethylenes (LDPEs), polyamides (e.g., Vestamid®), polyetherether ketones (e.g., PEEK™), VESTAMID® (e.g., Nylon 12), or combinations of these materials. In certain embodiments, inserts 52 are made of a metal or an alloy, such as, for example, stainless steel, Nitinol and/or platinum and combinations of these materials. Inserts 52 can be radiopaque or can include radiopaque markers.

Outer member 14, catheter 12, and bumper 70 can be formed of a polymeric material. Exemplary materials include those listed above with respect to inserts 52. In some embodiments, outer member 14 and/or catheter 12 is a composite including, e.g., a reinforcing member, such as a braid or coil. Although transition portion 17 of outer member 14 has tapered outer and inner diameters, other geometries may be used or transition portion 17 may be omitted altogether. Bumper 70 can be radiopaque and/or can include one or more radiopaque markers. Tip 61 is typically formed of a relatively soft polymeric material, which can be radiopaque and/or include one or more radiopaque markers.

In some embodiments, proximal tube portion 63 is formed by extrusion. For example, a polymeric material can be extruded with a shape generally corresponding to the cross section of tube portion 63 seen in FIG. 4b. Inserts 52 can be secured with respect to sockets 50 of tube 62 by, e.g., mechanical securing, such as by a press fit between tongue 54 and socket 50. Alternatively, or in addition, inserts 52 can be secured within sockets 50 by adhesive. In some embodiments, proximal tube portion 63 and inserts 52 are formed by co-extrusion. For example, an extruder can be configured to simultaneously extrude first and second materials. The first material is extruded with a cross section corresponding to proximal tube portion 63. The second material is extruded with a cross section corresponding to inserts 52. Other techniques besides extrusion can be used to fabricate proximal tube portion 63, inserts 52, or features thereof. For example, sockets 50 can be formed by machining a tube using, e.g., laser machining or mechanical cutting tools.

While each insert 52 has been shown as having an arcuate outer surface 58, other insert outer surface geometries are possible. Referring to FIG. 5a, an insert 152 has a projecting portion 156 and tongue 54. Projecting portion 156 defines shoulders 169 and has a generally triangular outer surface 158, which terminates in a point 160, which may be dull or rounded. When tongue 54 of insert 152 is disposed within socket 50 of tube 62, outer surface 158 creates a smaller contact area between the insert and inner surface 81 of outer member 15 than the contact area created by outer surface 58 of insert 52. In some embodiments, the smaller contact area can result in a lower withdrawal force of outer member 14 and/or can provide more area for fluid to flow between outer member 14 and tube 62.

Referring to FIG. 5b, an insert 256 has a projecting portion 256 and a tongue 54. Projecting portion 256 defines shoulders 269 and has a generally flat outer surface 258 bounded by edges 260. When tongue 54 of insert 252 is disposed within socket 50 of tube 62, outer surface 258 contacts the concave inner surface 81 of outer member 15 at a plurality locations, e.g., along edges 260. Portions of flat outer surface 258 spaced inward from edges 260 generally do not contact the concave inner surface 81. Hence, outer surface 258 distributes forces over a greater portion of the inner surface 81 than does outer surface 158 without significantly increasing the contact area between inserts 252 and inner surface 81. By distributing the forces, deformation, e.g., buckling, of outer member 14 can be reduced.

Figure 5C:
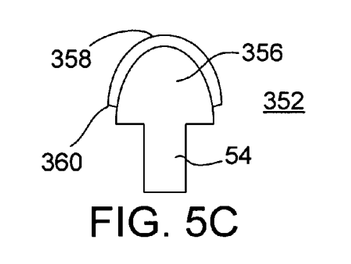

While the inserts discussed above are defined by a unitary piece of material, an insert may be a composite including more than one material. Referring to FIG. 5c, an insert 352 includes a tongue 54 and a projecting portion 356 having an outer surface 358 defined by an outer layer or coating 360. In general, coating 360 is formed of a lubricous material, e.g., a material that has a lower coefficient of friction with respect to inner surface 81 of proximal outer member portion 15 than a coefficient of friction of insert 352 and/or proximal tube portion 63 with respect to inner surface 81.

The outer layer or coating of the insert may be softer than a remaining portion of the insert. The harder portion of the insert provides radial compression resistance while the outer layer reduces friction with respect to the outer member. In some embodiments, an outer layer is adhesively bonded to the remaining portion of the insert.

In some embodiments, physical properties, e.g., lubricity and/or hardness, of the outer surface of the insert itself are modified with respect to other portions of the insert. For example, thermal techniques or chemical techniques, e.g., etching surface modification techniques, can be used to provide an insert with a lubricious outer surface without applying a separate outer layer.

Figure 5D:
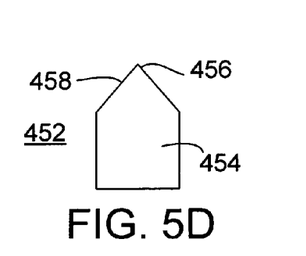

While the inserts discussed above have a projecting portion that is wider than a tongue of the insert, inserts can have other geometries. Referring to FIG. 5d, an insert 452 has a tongue 454 and a projecting portion 456, which is only about as wide as tongue 454. Hence, projecting portion 456 does not define shoulders that extend beyond tongue 454.

Figure 6:
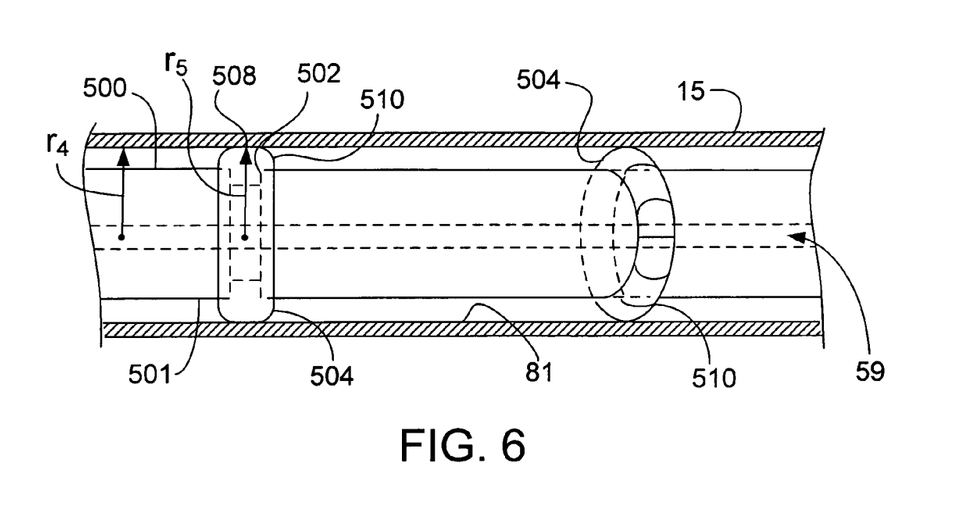
FIG. 6 is a partial side cross-sectional view of an embodiment of an endoprosthesis delivery system.

Although inserts 52 and sockets 50 have been shown as extending longitudinally along at least a portion of tube 62 (FIG. 4a), other insert and socket geometries are possible. For example, referring to FIG. 6, a tube 500 defines sockets 502, which are shaped as annular grooves extending circumferentially about an outer surface 501 of tube 500. A circumferential insert 504 is operatively associated with, e.g., partially disposed within, each socket.

Although maximum radial extent r2 of inserts 52 has been shown as being somewhat smaller than maximum radial extent r4 of inner surface 81 of proximal outer member portion 15 so as to define a gap Δg (FIG. 4b), other geometries are possible. For example, referring back to FIG. 6, a projecting portion 508 of each insert 504 has an outer surface 510 defining a maximum radial extent r5, which is about the same as radial extent r4 of proximal outer member portion 15. Hence, outer surface 510 contacts inner surface 81 such that no gap is defined.

In some embodiments, a socket and/or an insert can extend both circumferentially and longitudinally with respect to a tube, e.g., in helical fashion along at least a portion of the tube.

Although sockets and inserts have been described as elongated along at least one dimension, other shapes are possible. For example, referring to FIG. 7, a proximal tube portion 563 defines a plurality of sockets 550. Sockets 550 have a generally uniform, e.g., circular or peg-like, cross section. A tongue 554 of a respective insert 552 is disposed within each socket 550. Each tongue 554 has a shape generally complementary to the shape of socket 550. A cross section of sockets 550 and tongue 554 may have other shapes, e.g., polygonal or star-like.

Figure 7:
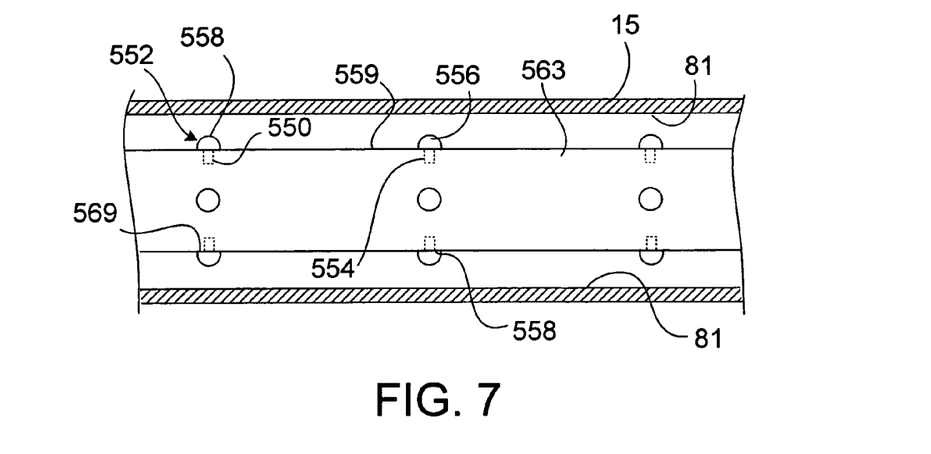
FIG. 7 is a partial side cross-sectional view of an embodiment of an endoprosthesis delivery system.

Each insert has a projecting portion 556 having a shoulder 569, which abuts an outer surface 559 of the proximal tube portion 563. Projecting portions 556 can limit or prevent contact between inner surface 81 of proximal outer member portion 15 and outer surface 559 of proximal tube portion 563. Inserts 552 can include a lubricious outer surface 558, which may be defined by, e.g., the insert itself, a coating, or a separate layer. An inner catheter of a system can include a plurality of such inserts spaced apart circumferentially and/or longitudinally along a tube of the catheter.

In some embodiments, an insert includes an outer surface that extends, e.g., longitudinally and/or circumferentially, but includes tongues that do not so extend. Instead, the tongues may be generally peg-like. Such inserts can be provided with more than one tongue so that the insert can be received within each of a plurality of spaced apart sockets.

FIG. 7 shows that the outer surface 559 of proximal tube portion 563, apart from sockets 550, has a generally uniform radial extent. For example, sockets 550 are not spaced apart by depressions as sockets 50 of proximal tube portion 63 are spaced apart by depressions 53. In general, an outer surface of a tube can, apart from sockets of the tube, define a generally uniform radial extent as does outer surface 559 of proximal tube portion 563 or can define one or more regions having differing radial extent as does outer surface 59 of proximal tube 63.

While tongue 54 of insert 52 is generally free of projections and socket 50 is shaped complementarily, inserts and sockets can have other configurations. For example, referring to FIG. 8, a proximal tube portion 763 includes a plurality of sockets 750, each defined by a pair of splines 753 extending along at least a portion of the proximal tube portion 763. A lateral dimension of each socket changes along a depth of the socket. A first portion 771 of each socket 753 has a first lateral dimension w1 and a second portion 773 of the socket has a second lateral dimension w2, which is greater than the first lateral dimension.

An insert 752 having a tongue 754 and a projecting portion 756 is operatively associated with each socket 750. A projection 777 of each tongue 754 generally complements a shape of second portion 773 of the socket. Although not apparent in FIG. 8, inserts 752 are elongated similar to inserts 52 of FIGS. 4a-4d. Hence, projections 777 are shaped as a pair of ridges extending along each tongue 754.

Figure 8:
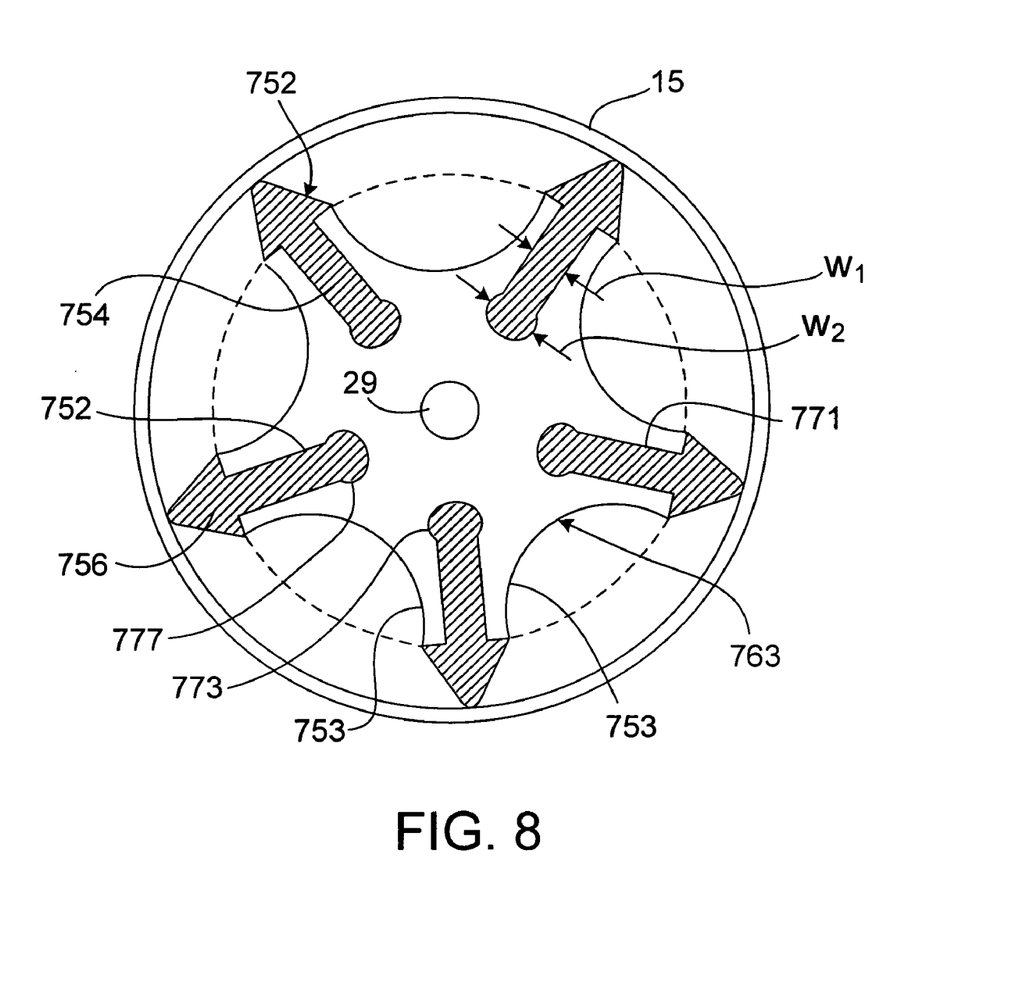
FIG. 8 is an end-on cross section through an embodiment of an endoprosthesis delivery system.

During assembly of proximal tube portion 763, tongue 754 is inserted into a socket 750. Projections 777 of tongue 754 spread splines 753 apart until projections 777 engage the second, wider portion 773 of the socket. Splines 753 then return to their original, unspread configuration. Engagement between projection 777 and second portion 773 of socket 750 helps secure insert 752 with respect to proximal tube portion 763.

Although tongues 754 have been described as elongated, a tongue with a projection may have other shapes. For example, the tongue may have a generally uniformly shaped cross-section along its length as described for inserts 552 and the projection may be shaped as, for e.g., a knob at an end of the tongue.

FIG. 8 shows that a tongue of an insert may completely fill a corresponding socket. Unlike insert 52, which leaves a void 61 at the base of tongue 54, inserts 752 completely fill sockets 750 such that no void remains.

While inserts discussed above have a greater radial extent than a tube in which they are received, an insert need not extend radially beyond the tube. For example, referring to FIG. 9, a proximal tube portion 663 has a plurality of sockets 650 each defined by a pair of splines 653. A maximum radial extent of proximal tube portion 653 is defined by a respective outer surface 667 of each spline 653. An insert 652 is disposed in each socket 650. Each insert has an outer surface 658, which has about the same radial extent as outer surfaces 667. Nonetheless, inserts 652 can reduce contact between proximal tube portion 663 and inner surface 81 of proximal outer member portion 15 by displacing and/or replacing some material of the outer surface of tube portion 663, e.g., the material that would otherwise be present in socket 650. As discussed for other inserts, outer surface 658 may be lubricious.

Figure 9:
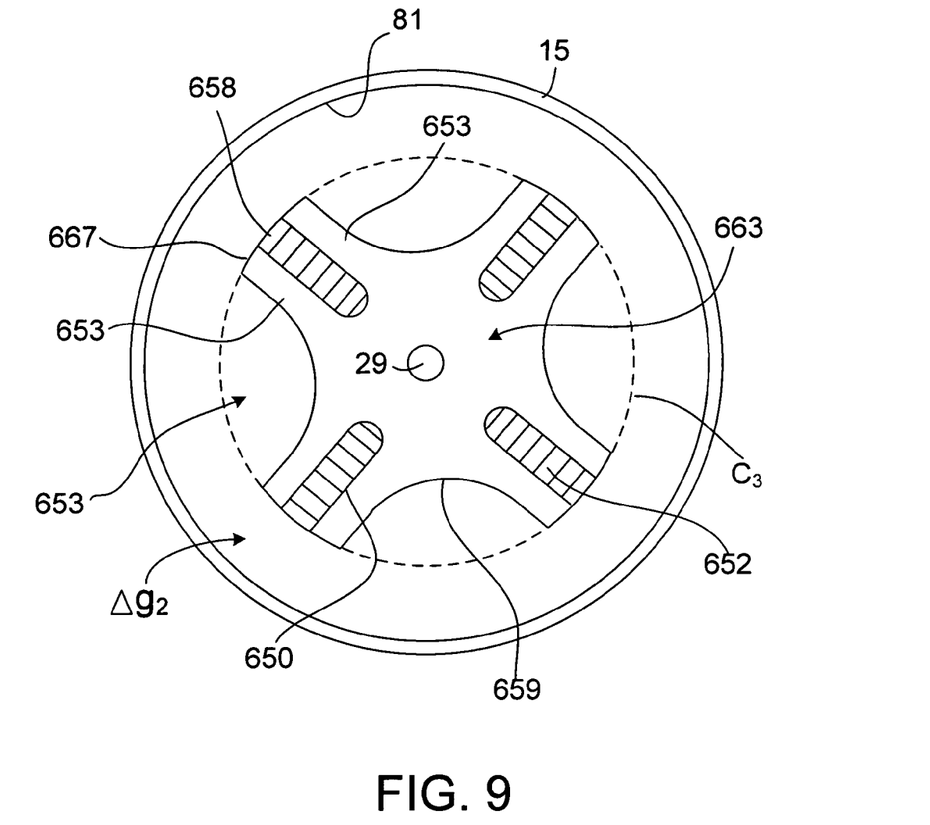
FIG. 9 is an end-on cross section through an embodiment of an endoprosthesis delivery system.

Outer surfaces 667 of splines 653 and outer surfaces 658 of inserts 652 define a circumference c3. A gap Δg2 is defined between inner surface 81 of proximal outer member portion 15 and circumference c3. Outer surface 659 of proximal tube portion 653 has a minimum radial extent that is smaller than a radial extent of outer surfaces 657 of splines 653. Adjacent pairs of splines are spaced apart by depressions 653 defined by outer surface 659. Depressions 653 can provide channels for fluid to flow between the outer member and proximal tube portion 653.

A comparison of FIGS. 4b, 8, and 9 also shows that the number of sockets and inserts is not limited to a particular number. Proceeding circumferentially around a tube, the number of sockets and inserts is generally at least 3 but can be larger, e.g., 4, 5, 6, or more.

A tube need not have inserts to reduce contact between the tube and the inner surface of the outer member. For example, referring to FIG. 10, a proximal tube portion 863 includes a plurality of outer layers 891 each having an outer surface 893, which is generally more lubricious than proximal tube portion 863 itself. Outer layers 891 are disposed over first outer surfaces 867 of proximal tube portion 863. The first outer surfaces have a radial extent that is greater than a radial extent of second outer surface portions 859 of the proximal tube portion. Layers can be integral with proximal tube portion 863, e.g., layers 891 and proximal tube portion 863 can be co-extruded. In some embodiments, layer 891 is a coating adhesively bonded to outer surfaces 867.

Figure 10:
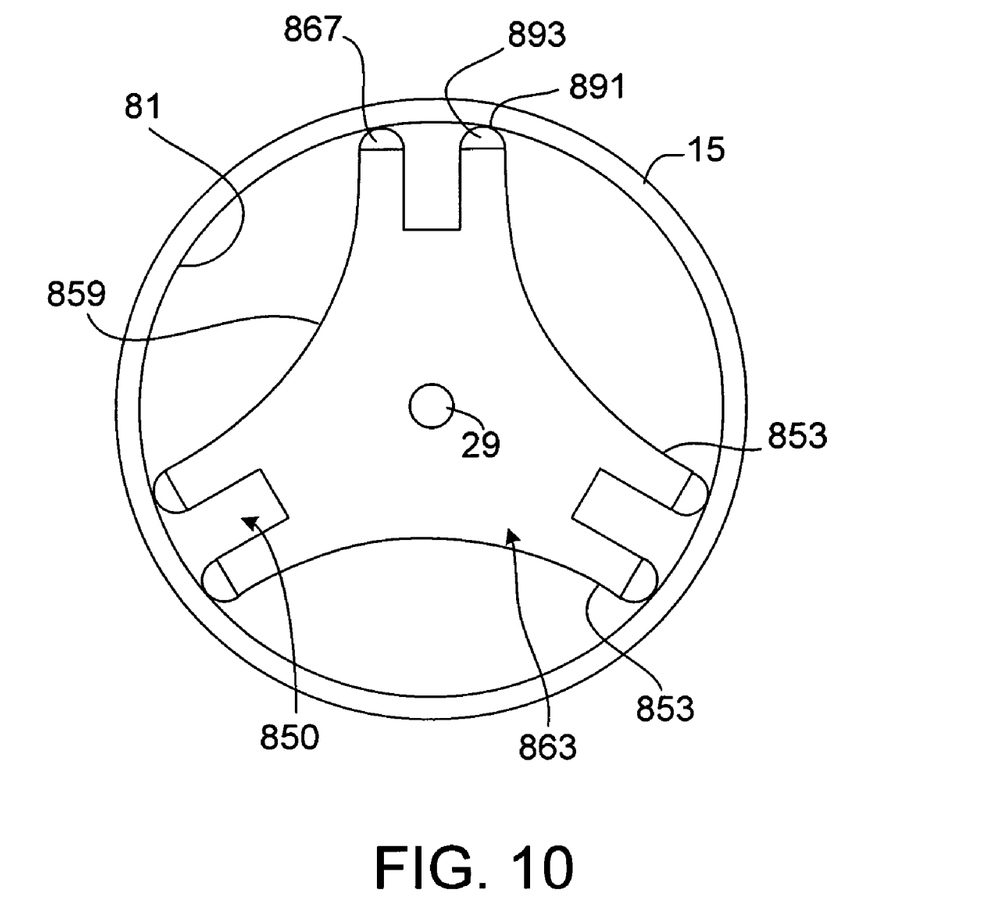
FIG. 10 is an end-on cross section through an embodiment of an endoprosthesis delivery system.

As shown in FIG. 10, proximal tube portion 863 has a plurality of pairs of splines 853, each pair of splines defining a respective socket 850. Splines 853 and sockets 850 can enhance the flexibility of proximal tube portion 863. In some embodiments, a respective insert is received within each socket 850. In some embodiments, sockets 850 are not present.

Figure 11:
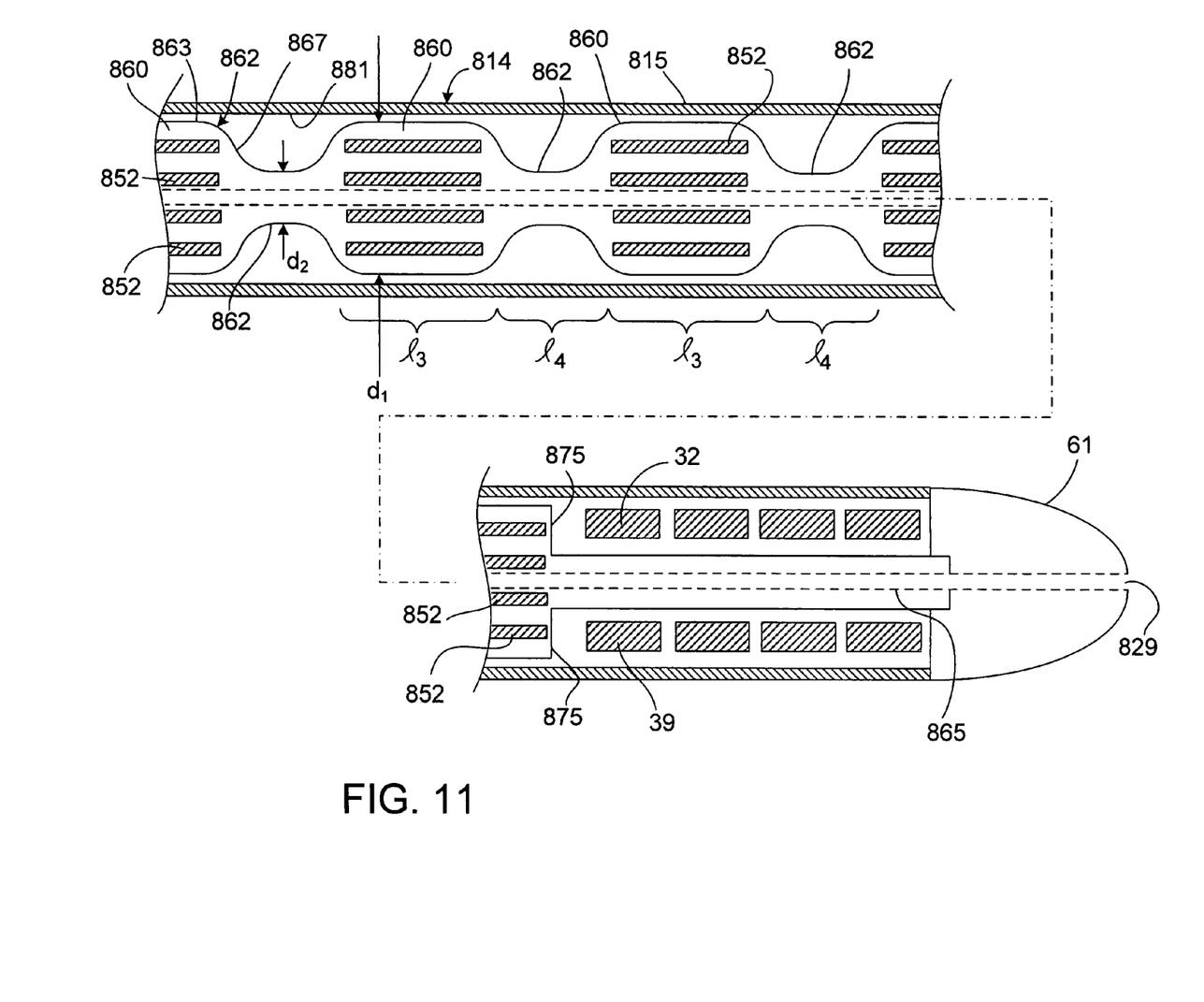
FIG. 11 is a partial mixed view of an embodiment of an endoprosthesis delivery system.

While FIG. 4a shows that proximal tube portion 63 has a generally constant radial extent proceeding along its length (as opposed to proceeding circumferentially), other tube geometries can be used. Referring to FIG. 11, a system 810 includes an outer member 814 and, at least partially surrounded by the outer member, an inner tube 862 having a proximal tube portion 863 and a distal tube portion 865. Stent 32 is disposed between an outer member distal portion 819 and distal tube portion 865. A guide wire lumen 829 extends through tube 862.

Proximal tube portion 863 includes a plurality of first sections 860 defining an outer diameter OD1 and a plurality of second sections 862 defining a smaller outer diameter OD2. A tapered, stress-reducing portion joins each first and second section. First sections 860 define a length l3 and second sections 862 define a length l4. In general, length l3 of first sections 860 is longer than length l4 of second sections 862. In some embodiments, a ratio of lengths l3 and l4 ranges from about 3 to about 20, e.g., the ratio can be about 10. In some embodiments, length l3 ranges from about 3 cm to about 15 cm, e.g., from about 5 cm to about 10 cm. In some embodiments, length l4 ranges from about 0.3 cm to about 1.5 cm, e.g., from about 0.5 to about 1 cm. Lengths l3 and l4 may vary along tube 862.

First and second sections 860 and 862 may be formed of different materials. For example, second section 862 can be formed of a polymeric material having a higher durometer than a material of first sections 860. Second sections 862 can include an outer layer, e.g., a layer of heat shrink tubing, to improve resistance to longitudinal compression and buckling.

Each first section 860 includes a plurality of inserts 852 disposed within respective sockets thereof. Inserts 852 can limit or prevent contact between an inner surface 881 of a proximal outer member portion 815. In FIG. 11, inserts 852 are almost as long as length l3 of first sections 860. However, inserts of first sections 860 can be substantially shorter than shown and may not be elongated at all as discussed for inserts 552.

FIG. 11 shows that a system need not include a separate bumper. In FIG. 11, some inserts 852 have distal ends 875, which extend to the end of proximal tube portion 863. Distal ends 875 are disposed and configured to abut proximal portion 39 of stent 32 to limit or prevent proximal movement of stent 32 during deployment.

While certain embodiments have been described, other embodiments are possible.

As an example, while systems having sockets and inserts extending along a proximal tube portion have been shown, sockets and inserts can extend along or be disposed along a distal tube portion. In use, such inserts can reduce contact between a stent and the distal tube portion. During loading the stent into the system and during deployment, such inserts can reduce the force required to move the stent with respect to the distal tube portion. In general, the inserts of a distal tube portion define a smaller radial extent than the radial extent r2 of the inserts of proximal tube portion 63.

As another example, while systems including a self-expanding stent have been described, other types of implantable medical endoprostheses can be used in the systems. For example, the implantable medical endoprosthesis can be a balloon-expandable implantable medical endoprostheses (e.g., a balloon-expandable stent). In such systems, inner catheter 12 would typically include an expandable balloon in the region around which the implantable medical endoprostheses is housed during delivery. Additional examples of implantable medical endoprostheses include stent-grafts and filters (e.g., arterial filters, venus filters).

Other embodiments are in the claims.

What is claimed is:
1. An endoprosthesis delivery system, comprising:
an inner member having an outer surface, the outer surface having a pair of splines extending therefrom, wherein the pair of splines has a socket formed therebetween;

an insert operatively associated with the socket, wherein a maximum radial extent of the insert is greater than a maximum radial extent of the inner member;

wherein at least a portion of the insert is disposed within the socket;

an outer member that at least partially surrounds the inner member and the insert, the outer member being slidable relative to the inner member and the insert, wherein the insert inhibits contact between the outer member and portions of the inner member adjacent the insert; and an endoprosthesis disposed between at least a portion of the inner member and the outer member.

2. The endoprosthesis delivery system of claim 1, wherein the inner member has a first lubricity and an outer surface of the insert has a second lubricity different from the first lubricity.

3. The endoprosthesis delivery system of claim 2, wherein the second lubricity is greater than the first lubricity.

4. The endoprosthesis delivery system of claim 2, wherein the insert includes an outer layer that defines the outer surface having the second lubricity.

5. The endoprosthesis delivery system of claim 1, wherein the portion of the insert having the greater radial extent is arcuate.

6. The endoprosthesis delivery system of claim 1, wherein the portion of the insert having the greater radial extent is triangular or conical.

7. The endoprosthesis delivery system of claim 1, wherein the insert is disposed so that the endoprosthesis surrounds at least a portion of the insert.

8. The endoprosthesis delivery system of claim 1, wherein the socket is a groove.

9. The endoprosthesis delivery system of claim 8, wherein the inner member has a distal opening and a proximal opening and the groove extends along the inner member for at least about 20% of a distance between the distal and proximal openings.

10. The endoprosthesis delivery system of claim 9, wherein the groove extends along the inner member for at least about 75% of a distance between the distal opening and the proximal opening.

11. An endoprosthesis delivery system, comprising:
an inner member having an outer surface, the outer surface having a pair of splines extending therefrom, wherein the pair of splines has a socket formed therebetween;
an insert operatively associated with the socket, wherein a maximum radial extent of the insert is greater than a maximum radial extent of the inner member;
an outer member that at least partially surrounds the inner member and the insert, the outer member being slidable relative to the inner member and the insert, wherein the insert inhibits contact between the outer member and portions of the inner member adjacent the insert; and
an endoprosthesis disposed between at least a portion of the inner member and the outer member;
wherein the socket is a groove;
wherein the inner member has a distal opening and a proximal opening and the groove extends along the inner member for at least about 20% of a distance between the distal and proximal openings; and
further comprising a plurality of inserts, wherein the inserts are spaced apart from one another along the groove.

12. The endoprosthesis delivery system of claim 9, wherein the insert extends along substantially all of a length of the groove.

13. The endoprosthesis delivery system of claim 8, wherein the groove has a longitudinal length of at least about 10 cm.

14. The endoprosthesis delivery system of claim 13, wherein the insert has a longitudinal length of at least about 5 cm.

15. The endoprosthesis delivery system of claim 1, wherein the inner member comprises one or more additional pairs of splines, and each pair of splines has a socket formed therebetween.

16. The endoprosthesis delivery system of claim 15, wherein the inner member comprises a plurality of depressions defined between adjacent pairs of splines.

17. The endoprosthesis delivery system of claim 16, wherein the depressions define a plurality of generally longitudinally extending channels extending between the outer member and the inner member.

18. The endoprosthesis delivery system of claim 1, wherein the insert extends around less than all of a circumference of the inner member.

19. The endoprosthesis delivery system of claim 1, wherein the inner member comprises a polymer.

20. The endoprosthesis delivery system of claim 1, wherein the insert comprises a polymer.

21. The endoprosthesis delivery system of claim 19, wherein the insert comprises a material selected from the group consisting of a fluoropolymer, a polyacetal, a polyamide, and combinations thereof.

22. The endoprosthesis delivery system of claim 1, wherein the insert comprises a radiopaque material.

23. The endoprosthesis delivery system of claim 1, wherein an outer circumference of a distal portion of the inner member is less than an outer circumference of a proximal portion of the inner member, at least the proximal portion comprising the socket.

* * * * *

UNITED STATES PATENT AND TRADEMARK OFFICE
CERTIFICATE OF CORRECTION

| | | |
|---|---|---|
| PATENT NO. | : 8,114,142 B2 | Page 1 of 1 |
| APPLICATION NO. | : 11/094022 | |
| DATED | : February 14, 2012 | |
| INVENTOR(S) | : Karen Larson et al. | |

It is certified that error appears in the above-identified patent and that said Letters Patent is hereby corrected as shown below:

Column 2
Line 50, delete "length l", and insert therefor -- length 11 --.

Signed and Sealed this
Twenty-fourth Day of April, 2012

David J. Kappos
*Director of the United States Patent and Trademark Office*